United States Patent [19]

Sones et al.

[11] Patent Number: 4,789,930

[45] Date of Patent: Dec. 6, 1988

[54] ENERGY DEPENDENT GAIN CORRECTION FOR RADIATION DETECTION

[75] Inventors: Richard A. Sones, Cleveland Heights; Karen L. Lauro, South Euclid, both of Ohio

[73] Assignee: Picker International, Inc., Cleveland, Ohio

[21] Appl. No.: 798,428

[22] Filed: Nov. 15, 1985

[51] Int. Cl.$^4$ ............................................. G01T 1/20
[52] U.S. Cl. ............................ 364/413.13; 250/361 R
[58] Field of Search ................... 364/414; 378/900, 19, 378/5, 99; 250/252.1, 255, 361 R

[56] References Cited

U.S. PATENT DOCUMENTS

| | | | |
|---|---|---|---|
| 3,848,130 | 11/1974 | Macovski | 378/100 |
| 3,965,358 | 6/1976 | Macovski | 378/5 |
| 4,029,963 | 6/1977 | Alvarez et al. | 378/5 |
| 4,035,651 | 7/1977 | LeMay | 364/414 |
| 4,068,306 | 1/1978 | Chen et al. | 364/414 |
| 4,070,707 | 1/1978 | Barber | 364/414 |
| 4,149,081 | 4/1979 | Seppi | 378/5 |
| 4,217,641 | 8/1980 | Naparstek | 364/414 |
| 4,228,515 | 10/1980 | Genna et al. | 364/414 |
| 4,472,823 | 9/1984 | Walthham | 364/414 |
| 4,497,061 | 1/1985 | Hounsfield | 364/414 |
| 4,540,882 | 9/1985 | Vinegar et al. | 250/255 |
| 4,571,491 | 2/1986 | Vinegar et al. | 378/5 |
| 4,628,688 | 12/1986 | Barnes | 250/486.1 |

OTHER PUBLICATIONS

Aaron Fenster, "Slit Xenon Detector for Tomochemistry in Computed Tomography" Jul. 1978.
Riederer, S. J., et al., "Limitations to Iodine Isolation Using a Dual Beam Non-K-Edge Approach", *Medical Physics* 8(1) Jan./Feb. 1981, pp. 54-61.
Lehman, L. A., et al., "Generalized Image Combinations in Dual kVp Digital Radiography", *Medical Physics,* 8(5), Sep./Oct. 1981, pp. 659-667.
Peschmann, K. R., "Xenon Gas Ionization Detectors", *Radiology of the Skull and Brain Technical Aspects of Computed Tomography,* vol. 5, Section III, pp. 4112-4126, 1981, the C. V. Mosby Company.
Wong, C. K., et al., "Calibration Procedure in Dual--Energy Scanning Using the Basis Function Technique", *Medical Physics,* 10(5), Sep./Oct. 1983, pp. 628-635.
Drost, D. J., et al., "A Xenon Ionization Detector for Scanned Projection Radiography: 95-Channel Prototype Evaluation", *Medical Physics,* 11(5), Sep./Oct. 1984, pp. 602-609.
Johns, P. J., et al., "Dual-Energy Mammography: Initial Experimental Results", *Medical Physics,* 12(3), May/Jun. 1985, pp. 297-304.

*Primary Examiner*—Jerry Smith
*Assistant Examiner*—Kimthanh T. Bui
*Attorney, Agent, or Firm*—Timothy B. Gurin

[57] ABSTRACT

A method and apparatus for calibrating the detector gain of a dual energy digital radiography system is provided. A basis material calibration object is scanned to create low and high energy pixel data. A regression is performed on the pixel data to derive at least one high energy calibration vector and at least one low energy calibration vector. The calibration vectors are transformed into high and low energy gain functions represented by a Taylor series expansion. An examination object is scanned to create low and high energy image data. The image data is combined with the gain function to create corrected low and high energy image data.

21 Claims, 3 Drawing Sheets

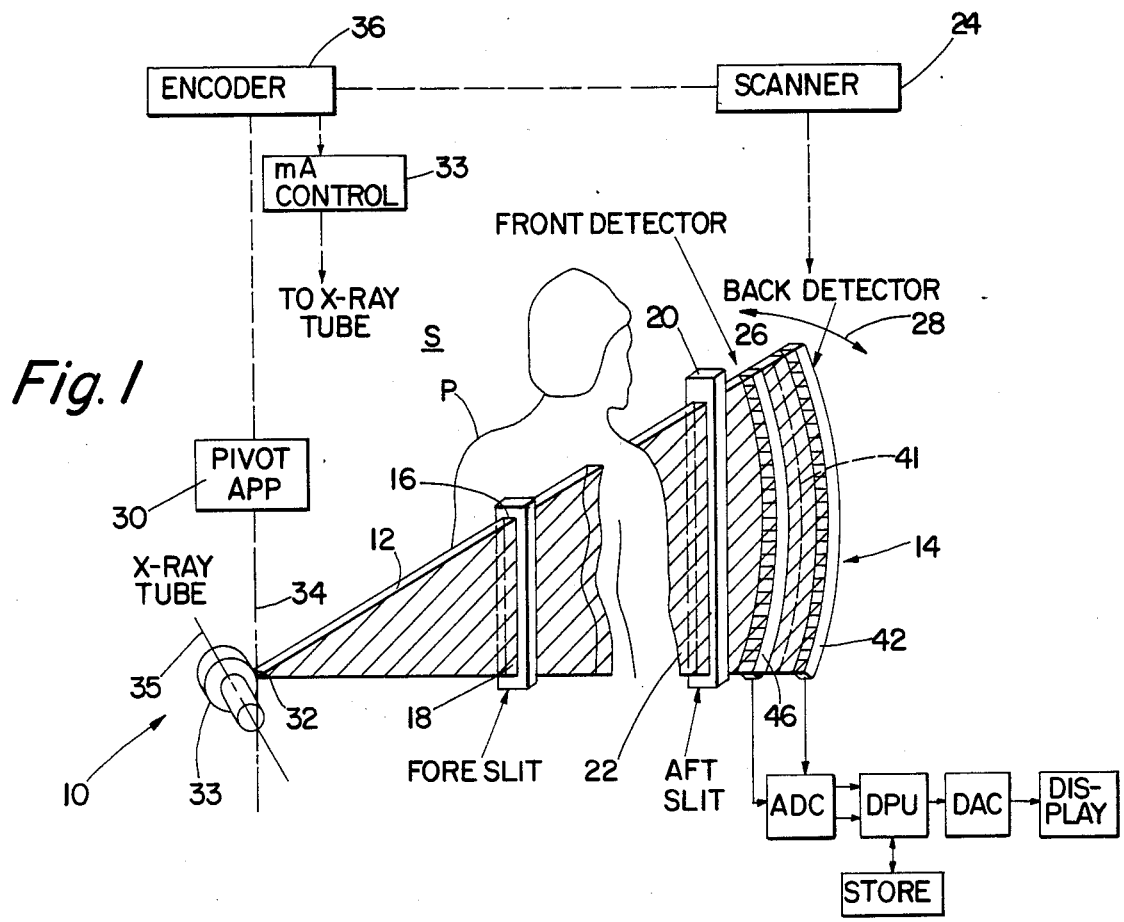
Fig. 1
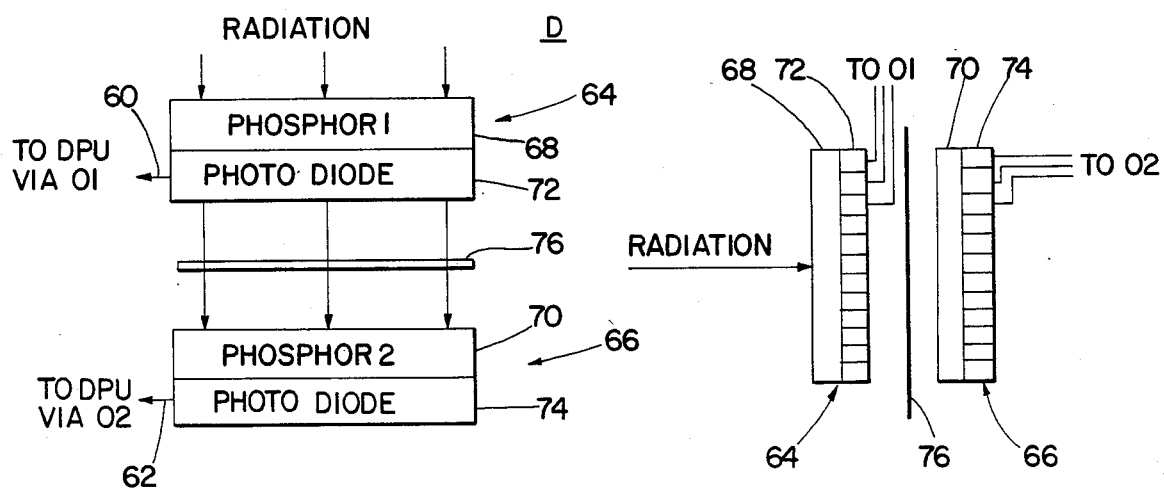
Fig. 2
Fig. 2A

ENERGY DEPENDENT GAIN CORRECTION FOR RADIATION DETECTION

DESCRIPTION

1. Technical Field

This invention relates generally to the field of radiation imaging and, more particularly, to a medical diagnostic digital radiography system having improved detector response. This invention deals with an energy dependent gain correction technique for realizing such improved response. It is to be appreciated, however, that the invention may find further application in conjunction with correcting detector response in other medical diagnostic equipment such as computed tomography scanners and the like.

2. Background Art

Radiography is a long known medical diagnostic imaging technique.

In a conventional radiography system, an X-ray source is actuated to direct a divergent area beam of X-rays through a patient. A cassette containing an X-ray sensitive phosphor screen and light and X-ray sensitive film is positioned in the X-ray path on the side of the patient opposite to a source. X-radiation passing through the patient's body is attenuated to produce a shadow image of a portion of the patient through which the X-rays pass.

More recently, digital radiography techniques have been developed. In digital radiography, the source directs x-radiation through a patient's body to a detector in the beam path beyond the patient. The detector, by use of appropriate sensor means, responds to incident radiation to produce analog signals representing the sensed radiation image, which signals are converted to digital information and fed to a digital data processing unit. The data processing unit records, and/or processes and enhances the digital data. A display unit responds to the appropriate digital data representing the image to convert the digital information back into analog form and produce a visual display of the patient's internal body structure derived from the acquired image pattern of radiation emergent from the patient's body. The display system can be coupled directly to the digital data processing unit for substantially real time imaging, or can be fed stored digital data from digital storage means such as tapes or discs representing patient images from earlier studies.

Digital radiography includes radiographic techniques in which a thin fan beam of x-rays is used, and other techniques in which a more widely dispersed so-called "area beam" is used. In the former technique, often called "scan (or slit) projection radiography" (SPR) a vertically oriented fan beam of x-rays is directed through a patient's body. The fan is scanned horizontally across the patient, or the patient is movably interposed between the fan beam x-ray source and an array or column of individual cellular detector segments which are aligned along an arcuate or linear path. Relative movement is effected between the source-detector arrangement and the patient's body, keeping the detector aligned with the beam, such that a large area of the patient's body is scanned by the fan beam of x-rays. Each of the detector segments along the array produces a row of signals indicating characteristics of the received x-rays along the row.

These analog signals are digitized and fed to a data processing unit which operates on the data in a predetermined fashion to actuate display apparatus to produce a display image representing the internal structure and/or condition of the patient's body.

In use of the "area" beam, a divergent beam of x-ray is directed through the patient's body toward a relatively large rectangular detector which is positioned opposite the patient with respect to the source. The detector covers a relatively expansive portion of the patient's body. The area beam diverges from the source to expose the radiation detector simultaneously over its entire face. The detector signals are digitized, fed to a data processing unit, and subsequently converted to a tangible representation of the patient's internal body structure or condition.

One of the advantages of digital radiography is that the digital image information generated from the emergent radiation pattern incident on the detector can be processed, more easily than analog data, in various ways to enhance certain aspects of the image, to make the image more readily intelligible and to display a wider range of anatomical attenuation differences.

Details of certain aspects of digital radiography systems such as described here are set forth in the following publications, hereby expressly incorporated herein by reference:

Mattson, R. A., et al., "Design and Physical Characteristics of a Digital Chest Unit, S.P.I.E. Volume 314, *Digital Radiography* (1981);

Arnold, B. A., et al., "Digital Radiography: An Overview", *Proc. of S.P.I.E.*, Volume 273, March 1981;

Kruger, R. A., et al., "A Digital Video Image Processor for Real Time X-Ray Subtraction Imaging", *Optical Engineering*, Volume 17, No. 6, (1978);

U.S. Pat. No. 4,626,688 issued Dec. 2, 1986 to Gary L. Barnes, entitled "Split Energy Level Radiation Detection";

U.S. patent application Ser. No. 542,384, filed Oct. 17, 1983, to Mattson, et al., entitled "Improving Signal Characteristics in Digital Scan Projection Radiography"; and U.S. Pat. No. 4,383,327 issued May 10, 1983 to Kruger entitled Radiographic Systems Employing Multilinear Arrays of Electronic Radiation Detectors.

In any radiation imaging system utilizing discrete detectors, such as computed tomography (CT) or digital radiography (DR), each detector's response to radiation varies slightly from a hypothetical ideal detector. If uncorrected, the image of an object of homogeneous material and constant thickness appears streaked rather than uniform. Detector non-uniformities may be mechanical, chemical, or electrical in nature, and may vary slowly with time, temperature, humidity and other environmental factors. In conventional CT and DR systems, detector nonuniformities are assumed to be independent of the object being scanned and corrections for the nonuniformities are implemented on a detector-by-detector basis. In general, the corrections to detector response are made possible by automatically measuring the actual performance of each detector prior to image data collection, so that during (or after) data collection this information may be used to mathematically normalize respective detector response to a hypothetical ideal detector.

Typically, CT and DR systems have detectors which respond linearly to radiation intensity but have slightly nonuniform slopes and y-intercepts. Three corrections are generally needed in such systems; namely, offset (background, y-intercept), drift and gain (slope) corrections.

For example, in a DR system offset correction is required due to system offset voltages and currents. These offsets are generally stable for the duration of a scan. Prior to each scan, the offsets are measured by reading detector response in the absence of radiation and are stored as a calibration vector represented as OFFSET (ROW). During each scan, the stored offset values are subtracted from the raw (uncorrected) pixel data, yielding offset corrected pixels. The offset correction is represented as follows;

$$\text{OFFSET CORRECTED PIXEL (ROW, COL)} = \text{RAW PIXEL (ROW, COL)} - \text{OFFSET (ROW)} \quad (1)$$

The offset correct pixels represent what the detectors would have produced if they behaved ideally, i.e., had zero offsets.

One of the advantages of digital radiography compared to conventional radiography is its potential for providing quantitative attenuation data. In order to meet this goal, DR systems must be calibrated so that the pixel values may be interpreted in absolute units. However, because of inevitable variations in detector response that occur with time, temperature, humidity and other environmental factors, such systems tend to drift out of calibration. Frequent recalibration (daily) minimizes drift to an acceptable level. It is at times, however, inconvenient to perform the calibration as frequently as is needed to keep drift negligible. In these cases, a drift correction is required which compensates for variations in system response from the time of last calibration.

The information which is required to perform drift correction is obtained by doing periodic (e.g., daily or hourly) airscans. An airscan is a scan taken with no object in the beam path. If the system does not drift, all airscans will produce identical data. If the system does drift, the airscans will differ and will provide a measure of the amount of drift of each detector.

An airscan is taken at the time of calibration and periodically thereafter. The mean offset corrected pixel value of each row of the calibration airscan is calculated and stored as a calibration vector represented as CAL ROW MEAN (ROW). Each subsequent airscan produces an analogous vector represented as ROW MEAN (ROW). A drift correction factor is calculated as follows:

$$\text{DRIFT (ROW)} = \frac{\text{CAL ROW MEAN (ROW)}}{\text{ROW MEAN (ROW)}} \quad (2)$$

Multiplying the offset corrected pixel value (Equation 1) by the drift correction factor (Equation 2) yields an offset, drift corrected pixel value that would be produced by driftless, zero-offset detectors.

The third correction which is typically applied in DR systems is gain correction. Gain correction factors are determined from the ariscan data taken at the time of calibration and are calculated as follows:

$$\text{GAIN (ROW)} = \frac{\text{CAL ROW MEAN (ROW)}}{\text{CAL IMAGE MEAN}} \quad (3)$$

Where CAL IMAGE MEAN is the mean (offset corrected) pixel value of the calibration airscan image. The fully corrected pixel value is achieved by multiplying the gain correction factor (Equation 3) by the offset, drift corrected pixel value. The final fully corrected pixel values are given by:

$$\text{PIX (ROW, COL)} = \text{OFFSET COR PIX (ROW, COL)} \quad (4)$$
$$*\text{DRIFT (ROW)} *\text{GAIN (ROW)}$$

These values are substantially equivalent to those produced by detectors with no drift, zero offset and gain identical to the mean gain of the actual detectors.

It should again be noted that the above described techniques correct for system and detector nonuniformities and do not take into account nonuniformities in detector response which are dependent on the object being scanned.

Dual energy digital radiography is a well-known technique capable of generating what is known as material specific images. The material specific images are generated from a pair of images acquired substantially simultaneously at two different X-ray energies. Details of certain aspects of obtaining material specific images are set forth in the following publication, hereby expressly incorporated by reference:

Lehmann, L. A., et al., "Generalized Image Combinations in Dual kVp Digital Radiography,", *Medical Physics,* Volume 8, No. 5, pp. 659–667, September/October, 1981.

The material specific image concept is based on the fact that different materials exhibit different relative attenuation depending on X-ray beam energy. A given material can be identified if the Compton scatter and photoelectric absorption components of its attenuation coefficient are known, since these are the two main absorption processes in the energy range used in diagnostic imaging (40–110 keV). Compton scatter is the dominant attenuation process of low atomic weight materials, such as water, soft tissue and Plexiglas TM, while photoelectric absorption dominates for high atomic weight materials, such as bone, calcium and aluminum.

A dual energy system based on an energy discriminating radiation detector (as opposed to one based on kVp switching) has been proposed. See the above incorporated patent by Barnes. The incident X-ray spectrum is held constant and different thickness combinations of two basis materials—usually Plexiglas TM and aluminum—are scanned. The resulting high and low energy image pixel values fully characterize the material-thickness to sensor-signal transfer function of the system. Because the Compton and photoelectric energy dependencies are universal, characterization with respect to two basis materials is all that is required to deduce the thickness/signal relationship of any other material. Looked at from another perspective, for a given incident beam quality, the beam quality emerging from any object is uniquely and fully determined by the values of the high and low energy pixel values.

Experience with DR systems indicates that the application of conventional offset, drift and gain correction techniques described above is not sufficient to completely remove image streaking. Study of the effect reveals that it is largely due to variations of detector response with X-ray beam spectral distribution (beam quality). Since X-ray beam quality is dependent on the imaged object's thickness and composition, beam quality and thus detector response varies from pixel-topixel. Detectors which respond identically at one beam quality may exhibit slightly different gains at another beam quality, leading to image streaks as object attenuation varies from location to location.

Consider a dual energy digital radiography system, based on an energy discriminating radiation detector as proposed by Barnes. At a given beam quality, detectors of this sort respond linearly to X-ray intensity. For example, for a fixed geometry and beam filtration, detectors A and B may have identical (offset, drift and gain corrected) responses of 1 nA/(mR/sec). However, if the object is changed (i.e., beam filtration is changed), beam quality changes and the responses of detectors A and B may become, say, 1.1 nA/(mR/sec) and 1.2 nA/(mR/sec), respectively.

Some of the causes of gain dependence on beam quality are readily understood. First, the phosphor screen may vary in thickness of composition. Second, the photodiode substrate materials and metalization (through which the X-ray beam passes to strike the rear detector) may not be uniform. Third, the front and back photodiode arrays are each comprised of 32 identical integrated circuit subassemblies. Where these subassemblies abut, X-ray transmission is somewhat different than elsewhere, leading to anomalous beam quality behavior of the subassembly end detectors. Other causes of gain dependence on beam quality may exist, but have not yet been identified.

It is therefore an object of this invention to overcome the above-referenced problems and others through normalizing the response of a radiation detector for variations in beam quality by using the image pixel values to modify the detector response.

SUMMARY OF INVENTION

The disadvantages of the prior art as described above are reduced or eliminated by a digital radiography imaging system and method incorporating novel energy dependent gain correction technique for realizing improved detector response.

In accordance with one aspect of the present invention a method is provided for calibrating a dual energy digital radiography system. A basis material calibration object is scanned to create low and high energy pixel data. A regression is performed on the pixel data to derive at least one high energy calibration vector and at least one low energy calibration vector. The calibration vectors are transformed into high and low energy gain functions. An examination object is scanned to create low and high energy image data. The image data is then combined with the gain functions to create corrected high and low energy image data.

In accordance with another aspect of the present invention a medical imaging system is provided. A radiation source and detector array spaced sufficiently from the source to accommodate the placement of an object between the source and the detector is provided. A scanning means scans the detector array relative to the object while maintaining alignment with the radiation source. Power means is employed for actuating the source to direct radiation through the object and toward the detector array during scanning. The array comprises a number of detector elements, each being responsive to incident radiation to produce electrical signals indicative of radiation. Circuitry coupled to the detector array responds to these signals and determines the beam quality of the radiation incident on the detector array. Correction means coupled to the circuitry and the detector array corrects the response of the detector array to incident radiation by a function of the beam quality of the incident radiation. Imaging circuitry coupled to the correction means responds to the corrected electrical signals to generate an image of internal structure of the object as evidenced by a radiation pattern emergent from the object and incident on the detector array.

In accordance with a more limited aspect of the present invention a first set of calibration signals representative of the detectors response to variations in beam quality are stored. A function generator produces a gain correction function by combining the set of calibration signals with a set of image signals representative of radiation transmitted through the object under examination. Circuitry modifies the image signal set by the gain correction function to produce a gain corrected detector response.

In accordance with yet another aspect of the present invention, a method is provided for gain correcting the response of a radiation detector. A first detector response is determined by measuring detector response to radiation transmitted through basis material wherein the transmitted radiation is in at least two energy ranges. A representation of beam quality of the transmitted radiation is determined by performing a regression on the first detector response. A gain correction function which is dependent on the beam quality of the transmitted radiation is determined. A second detector response to radiation transmitted through an object to be imaged is determined. The second detector response is combined with the gain correction function to gain correct the second detector response.

One advantage of the present invention is that variations in detector gain due to changes in beam filtration are normalized by correcting the detector response as a function of beam quality.

Yet another advantage of the present invention is that variations in detector response due to variations in the composition of the object being imaged are corrected by utilizing image data taken from the detector while the object is imaged.

Yet another advantage of the present invention is that it provides for substantially real time gain correction of the detector response.

These and other aspects of the present invention will become apparent upon reading and understanding the following detailed description of the preferred embodiment.

BRIEF DESCRIPTION OF THE DRAWINGS

The invention may take form in various steps and arrangements of steps or in various components and arrangement of components. The drawings are only for the purpose of illustrating a preferred embodiment and are not to be construed as limiting it.

FIG. 1 is a perspective view of a digital radiography system incorporating the present invention;

FIG. 2 is a side view illustrating a portion of the system illustrated in FIG. 1.

FIG. 2A is a detailed side view illustrating a portion of the system in FIG. 1.

BEST MODE FOR CARRYING OUT THE INVENTION

Figure 3:
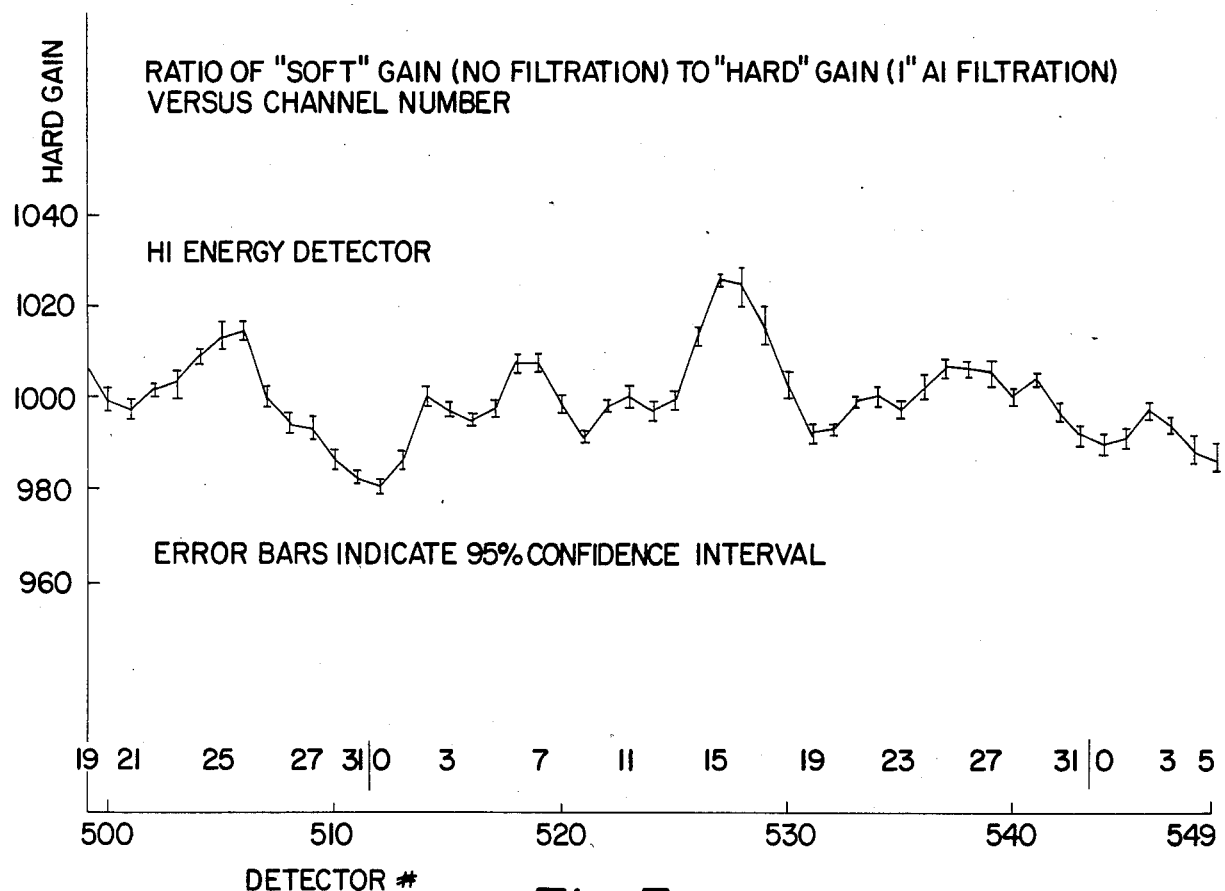
FIG. 3 is a graphical representation of detector gain as a function of beam quality.

A system S for performing digital scan projection radiography (SPR) is illustrated in general form in FIG. 1. The system S directs a beam of penetrative radiation, preferrably X-rays through a patient P and produces, from information borne by the X-ray pattern emergent from the patient's body, a representation, generally in the form of a visible image, describing internal structure or condition of the patient's body.

The system S incorporates an X-ray source 10 for directing a beam of X-ray energy illustrated as a collection of rays 12 through the patient P and onto a detector assembly 14. A first collimator structure 16 defines a generally vertical fore slit 18 for collimating the X-rays emanating from the source into a spread beam lying generally within a vertical plane. A second collimator structure 20 defines an aft slit 22 located between the patient and the detector assembly, aligned with the fore slit and with the detector, for enhancing this collimation.

Mechanical structure (not shown) maintains a mutually constant relative alignment between the collimators 16, 20, the X-ray source 10 and the detector assembly 14 and provides means for scanning the collimators and detector in unison relative to the patient's body in a manner described in more detail below.

The mechanical structure can suitably comprise a gantry structure of known configuration (not shown) which physically holds the collimators and detector in a rigid alignment, and mechanical drive means to move the entire gantry to effect scanning. Alternately, the components can be coupled to individual drive mechanisms, and servo techniques can be employed in known fashion to maintain the desired alignment during scanning motion.

In the preferred embodiment, mechanical scanner apparatus 24 is coupled to the detector assembly 14 to move the detector along a generally arcuate path defined by the arrows 26, 28. The arcuate path is centered about a vertical axis 34 through a focal spot 32 of the tube 10, described in more detail below.

Pivoting apparatus 30 is coupled to the X-ray source. The apparatus 30 pivots the source, synchronously with detector and collimator arcuate motion, to continuously track the detector 14 and the mutually aligned collimators 16, 20.

The X-ray source 10 comprises an X-ray tube, and associated power circuitry (not shown) for electrically actuating the tube to produce X-rays (in pulsed or continuous mode) emanating from a focal spot 32 defined by the structure of the tube. Tube 10 produces X-rays by directing a stream of electrons onto an anode 33 of the tube, the anode rotating about an axis 35. The pivoting motion effected by the pivot apparatus 30 causes the tube to pivot about the vertical axis 34 extending through the focal point 32.

It is believed preferable to couple the detector assembly 14 to the master drive of the scanner apparatus 24 and to control the tube and collimators to follow, since detector positioning is more critical than tube positioning.

An encoder 36 is coupled to the scanner apparatus 24 and produces a signal indicating the instantaneous position of the detector 14 along its arcuate path described by the arrows 26, 28. The output of the encoder 36 is directed to the pivot apparatus 30 for synchronizing the pivoting motion of the X-ray tube 10 with the arcuate motion of the detector 14 and collimators 16, 20, to maintain continuous alignment between the X-ray beam, collimators and detector assembly during scanning motion.

An example of a type of encoder apparatus is described in U.S. Pat. No. 4,015,129, issued on Mar. 29, 1977 to Manring, et al., incorporated expressly here by reference, and owned by the assignee of the present application.

The detector assembly 14 includes an array of individual detector elements. Each of the detector elements responds to light energy (generated by X-rays as described below) to produce an analog electrical charge signal which represents a characteristic of the X-rays which caused the production of the electrical signal.

The detector includes a first (front) array 40 of detector elements and a second (back) array 42 of detector elements located behind the first array with respect to the X-ray tube. Both the first and second arrays are aligned with the fore and aft slits. Radiation from the X-ray tube falls upon, and is partially absorbed by, the first array, and the remainder of the radiation, passing through the first array, falls upon and is detected by the second array. In this way, separate dual energy response is obtained, as explained in the Barnes patent incorporated above.

Each of the arrays includes a single line or column of detector elements arranged along an arcuate path defined by a portion of a circle having its center located at a focal spot 32 of the X-ray tube. This geometry reduces the nonuniformity of the X-ray energy across the beam set 12 propagating through the collimator 16, 20. An example of one such focussed detector array can be found in co-pending U.S. patent application to Sones, Ser. No. 673,779, filed Nov. 21, 1984, which is owned by the present assignee and is expressly incorporated herein by reference.

Each detector element comprises a photodiode. Overlaying each photodiode is a scintillation material responsive to X-rays to produce visible light energy. Preferably, the scintillation material used in connection with the first array differs from that used in connection with the second array. The scintillation material associated with the first array is selected for its ability to absorb and produce light in response to X-rays from the source falling primarily within a relatively low energy range. The higher energy X-rays pass through the first array and fall on the second array, causing the scintillation material associated with the second array to produce light which is detected by the individual detector photodiodes of the second array. Suitable types, thicknesses and physical configurations of the scintillation material are defined in the above incorporated Barnes patent.

In operation, the detector, collimators and X-ray tube are moved to the left as in the direction illustrated by the arrow 26 to prepare for a scan. In performing a scan, the X-ray tube is actuated to produce X-ray energy. The scanner apparatus 24 and pivot apparatus 30 cooperate to synchronously scan the vertical spread beam of X-rays from left to right as shown in FIG. 1. Upon completion of a scan each detector element creates a row of image data. For calibration purposes, scans can be taken without any object in the beam path. These calibration scans are commonly referred to as airscans. For imaging an object (typically a patient), the spread beam of radiation is scanned across the object. During either scanning motion, the detector elements of the detector assembly 14 produce analog electrical signals.

The detector 14 separately detects X-rays of different energy ranges impinging on the detector array. An element of the detector array, by way of two sets of leads 01, and 02, transmits analog signals representing detected X-rays within lower and higher energy ranges, respectively.

The signals on the lead sets 01, 02, are provided to an analog-to-digital converter (ADC) which digitizes the outputs and feeds them to a digital processing and receiving unit (DPU). The DPU processes these digitized output signals to construct a digital representation of an image of the patient's internal body structure scanned by the X-ray beam 12, on a line-by-line basis. Digital signals from the DPU are converted to analog form by way of a digital-to-analog converter (DAC), and fed to a display unit, which in response, produces an image in visual form corresponding to the image representing signals from the DPU.

Optionally, digital storage means can be provided in conjunction with the DPU in order to digitally store the image representations for future use. In such event, the digitally stored signals can be played back through the DPU, converted to analog form, and their corresponding images displayed at a later time on the display apparatus.

FIG. 2 illustrates a particular layered detector segment structure for use as a component of an energy sensitive radiation detector array 14. The detector responds to radiation incident upon it to produce two outputs at leads 60, 62. The output at lead 60 represents radiation incident upon the detector segment having an energy level in a lower energy range. The output at the lead 62 represents the detector segment's response to incident X-ray radiation having an energy level in a second, higher energy range.

The detector segment includes a first elemental layer 64 primarily responsive to lower energy X-rays, and a second elemental layer 66 responsive to higher energy X-rays. Each of the layers 64, 66 includes a phosphor coating layer 68, 70, respectively, and a photodiode 72, 74, each respectively optically coupled to the phosphor layers 68, 70.

FIG. 2A shows how the detailed structure of FIG. 2 appears when incorporated into a linear detector array 14. FIG. 2A represents a side view of such an array.

FIG. 2A illustrates the two detector elements or layers 64, 66, one positioned behind the other with respect to the incident radiation from the source. Each element includes, respectively, a coating layer of phosphor 68, 70, and a set of photodiodes respectively indicated at 77, 74. Between the elements is located the filter element 76.

Each photodiode has a lead emergent therefrom for transmitting its analog radiation indicating signal, e.g., 60, 62, to the appropriate one of the lead groups 01, 02, as described generally above. For purposes of clarity, only representative leads are shown in FIG. 2A.

The application of the split energy radiation detector of this invention is by no means limited to a linear array of detectors, for use in slit projection digital radiography, the environment described in detail above. The present invention can also be embodied in a so-called "area" detector, i.e., a relatively large rectangular radiation detector covering a relatively expansive portion of the patient's body, designed for use with so-called "area" beams, which diverge from the source to expose the radiation detector simultaneously over its entire face. In this case, the phosphor matrix embodying the detector can consist of either single integral intensifying screen, a cellularized intensifying screen, or a cellularized matrix of individual scintillating crystals. Examples of these types of area detector can be found in the co-pending Sones application incorporated above.

Analog detector outputs from each of the detector elements are periodically sampled. Each sampling produces analog signals representing a portion of image information. Over the course of the scan from one side to the other side, signals are developed describing a plurality of image lines or rows, which together constitute an area image of the patient's internal body structure. The electrical signals are then digitized and processed to produce the desired patient image.

In a dual energy digital radiographic system as described above, it is possible to enhance the detector response to compensate for detector gain dependence on beam quality. As will be seen, the gain factor for each detector is not a constant but instead is a function of beam quality.

Experimental results with a dual energy DR system provide an example of the significance of the nonuniform gain dependence on beam quality. Scans were first taken with no object in the beam path (airscan). A second scan was then taken with one inch of aluminum filtration placed in the beam path. The gains of the detectors were measured and found to vary with filtration in a repeatable, statistically significant way. Referring to FIG. 3, the detector's gain is plotted as a function of beam filtration. For the rear high energy array, the gain of the detectors at the subassembly centers decreased about 2.5 percent when the aluminum filtration was added. The gain of the detectors at the subassembly ends increased as much as 1.9 percent. Hence, if all channels were gain normalized with no filtration, at a filtration of one inch of aluminum the respective gains would differ by as much as 4.4 percent. This difference in detector response is large enough to cause streak artifacts in the resultant image.

As pointed out above in the discussion on material specific images, the beam quality of the radiation incident on the detectors is uniquely determined by low and high energy pixel values (PIX LO, PIX HI), e.g., signals 60 and 62, repsectively, (see FIG. 2). Hence, the gain factor for each detector is a function of the low and high energy pixel values. The gain factor function, GAIN (PIX LO, PIX HI), may be effectively represented by a Taylor series expansion of the following sort:

$$\text{GAIN(PIX LO, PIX HI)} = A_0 + A_1^* \log(\text{PIX LO/Ref PIX LO}) + A_2^* \log(\text{PIX HI/Ref PIX HI}). \quad (5)$$

where;

$A_0$, $A_1$ and $A_2$ are constants characteristic of a given detector; Ref PIX LO and Ref PIX HI are the pixel value obtained (for the detector under consideration) at a reference (nominal) beam quality.

A Taylor series expansion is a well known mathematical technique as described in Calculus and Analytical Geometry by George B. Thomas, Jr., 4th edition, Addison and Wesley Publishing Co., 1968.

The constants $A_0$, $A_1$ and $A_2$ are vectors (i.e., $A_0 = A_0$ (Row), $A_1 = A_1$ (Row), $A_2 = A_2$ (Row)) calculated from the data which are acquired during system calibration. Dual energy systems must undergo "basis" calibration irrespective of whether an energy dependent gain correction is used. The same data acquired for basis calibration can be used to calculate $A_0$, $A_1$, and $A_2$ for energy dependent gain corrections.

A description of basis calibration is set forth in the following publication hereby expressly incorporated by reference:

Wong, C. K. et al., "Calibration Procedure in Dual Energy Scanning Using the Basis Function Technique," *Medical Physics*, Volume 10, Number 5, pages 628-635, 1983.

The following is a brief description of basis calibration in order to aid in the understanding of the present invention. Two so-called basis materials are selected. Plexiglas (or lucite) and aluminum are commonly chosen due to their low cost, availability and since they span the range of atomic numbers of biological tissues. Various combinations (the more combinations used, the more accurate the calibration) of plexiglas and aluminum are scanned and the corresponding low and high energy pixel values (or mean pixel values) are stored. A basis material calibration phantom suitable for performing the basis calibration described herein is disclosed in copending U.S. application Ser. No. 798,427 to Sones et al. entitled Radiation Imaging Calibration filed concurrently herewith and which is expressly incorporated herein by reference.

Let x and y represent thickness of plexiglas and aluminum respectively and let u and v represent low and high energy mean pixel values respectively. The dual energy basis functions may then be represented as;

$$x = f(u, v) \qquad (6)$$

$$y = g(u, v) \qquad (7)$$

The functions f and g are approximated from the measured data by a process known as regression. Regression is a well known mathematical technique as described in Data Reduction and Error Analysis for the Physical Sciences by Philip R. Bevington, McGraw-Hill, 1969, chapter 9 on Multiple Regression. See also the above reference Lehmann article.

Basis calibration data derived as described above as well as the regression concept is also used for the energy dependent gain calibration of the present invention.

For each plexiglas/aluminum combination which is imaged, the gains of all low and high energy detector elements are determined. This is done just as described in the "Background Art" section of this application for air scan gains, except plexiglas/aluminum scans are used instead. Hence, for each detector element, one can form (mean) low and high energy pixel values corresponding to that particular low/high energy pair of detector elements, along with the corresponding detector element gain.

In other words, the gain of a given detector element can be represented as;

$$\text{gain} = h(u, v), \qquad (8)$$

where u and v represent the low and high energy pixel values (PIX LO and PIX HI in Eq. (5)), respectively. The function h is approximated from the measured data by regression, that is, regression yields the values of $A_0$, $A_1$ and $A_2$.

It should be emphasized that the PIX LO and PIX HI values in equation 5 are offset and drift corrected in the conventional manner. The Ref PIX LO and Ref PIX HI values are offset corrected only since they are determined at the time of calibration.

The gain factor function calculated from equation 5 replaces the conventional gain factor discussed above for calculation of the final pixel value. Note that if the beam quality at the detector is the same as the reference or nominal beam quality, PIX LO=Ref PIX LO and PIX HI=Ref PIX HI and equation 5 reduces to:

$$\text{GAIN(PIX LO, PIX HI)} = A_0 \qquad (9)$$

Hence, at nominal filtration, the beam quality dependent gain correction of equation 5 reduces to the form of the conventional gain correction.

Equation 5 can be simplified to:

$$\text{GAIN (PIX LO, PIX Hi)} = A_3 + A_1 * \log (\text{PIX LO}) + A_2 * \log (\text{PIX HI}) \qquad (10)$$

where $$A_3 = A_0 - A_1 * \log (\text{Ref PIX LO}) - A_2 * \log (\text{ref PIX HI}).$$

The vector $A_3$ is a constant in the sense that it may be calculated at the time of calibration and stored.

Figure 4:
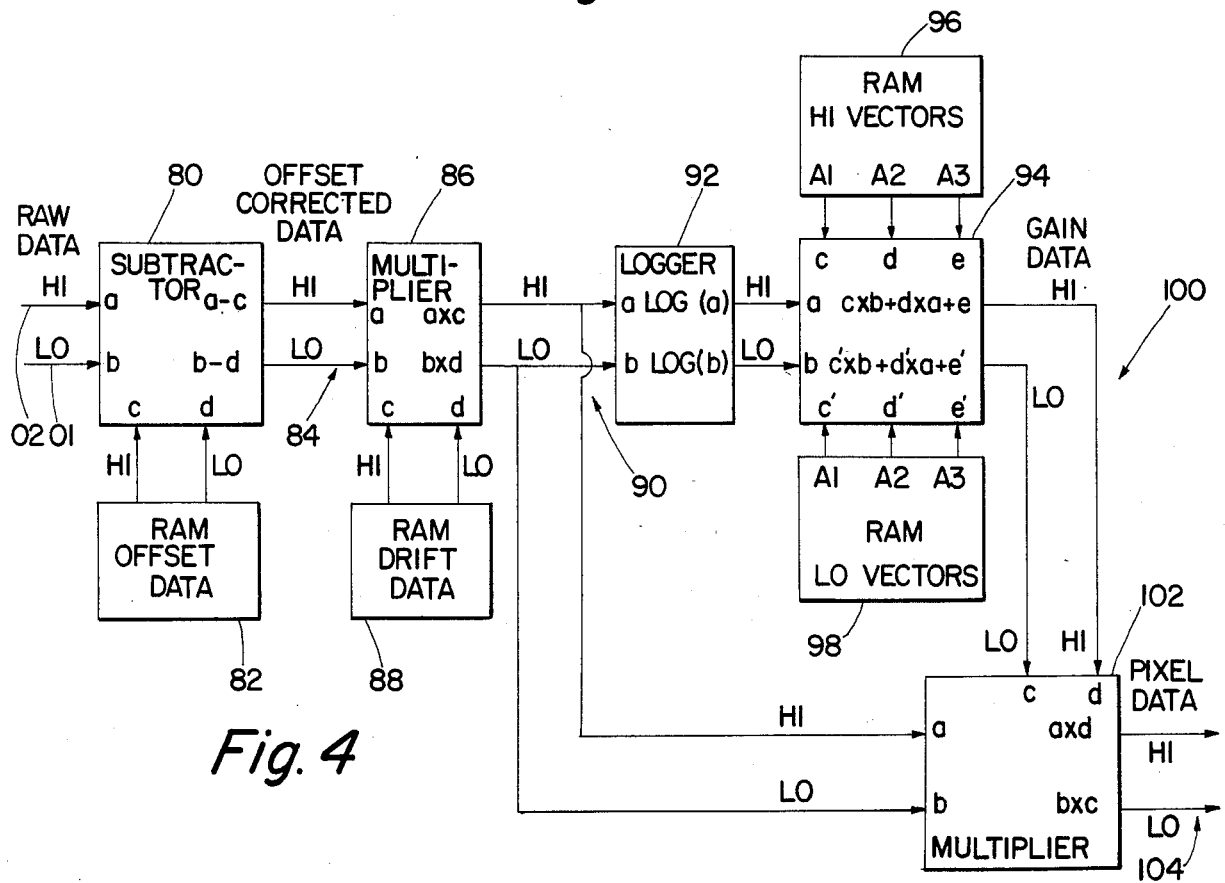
FIG. 4 is a block diagram of circuitry for implementing the present invention.

Turning now to FIG. 4, a block diagram of the circuitry for implementing the present invention is described. Raw uncorrected pixel data, taken from signal sets 01 and 02 are fed through a subtractor 80 where offset data stored in RAM 82 are subtracted from the raw pixel data to yield offset corrected data 84 (see equation (1) above). Offset corrected data 84 are fed through a multiplier 86 where they are multiplied by drift correction data stored in RAM 88, yielding offset and drift corrected data 90 (see equation (2) above). Offset and drift corrected data 90 are then fed through a logarithm generator 92 to a sum of products calculator 94 which performs the calculations of equation (10). The $A_1$, $A_2$ and $A_3$ vectors for the low and high detectors are stored in RAMs 96, 98. Gain correction data 100 emerges from the sum of products calculator 94 and goes to another multiplier 102 where they are multiplied by the offset and drift corrected data 90, yielding the final, fully corrected low and high pixel values 104 which are sent to the system display and/or storage device (see FIG. 1).

The arithmetic and memory subunits of the circuitry depicted in FIG. 4, as well as the required logic and timing electronics (omitted for clarity), could be readily configured by someone skilled in digital electronics from components commercially available. The logger 92 can be a RAM look-up table. Offset RAM 82 must be loaded prior to each scan with (averaged) raw data acquired without X-rays on. This could be accomplished by additional circuitry or by reading raw data into a host computer, averaging, and then downloading the result into offset RAM 82. The contents of the drift RAM 88 are calculated from a daily airscan, so the most convenient procedure is to store these data in a host computer and download them periodically. The remaining RAMs 96, 98 contain data calculated from the dual energy calibration, so, again, the most convenient procedure is to store these data in the host computer and download them periodically.

The circuitry of FIG. 4 is capable of "real time" data correction, in the sense that, if it is configured from readily available ICs, it will be fast enough to keep up with the data rates currently employed in dual energy DR systems (about 1 Mbyte/s). Hence, data are corrected "on the fly", and the corrected image may be viewed immediately after it is acquired.

The calculations described above and implemented by the circuitry of FIG. 4 could also be performed in a computer. However, because the number of pixels in DR images is large (about one million), processing by a general purpose computer tends to be slow. Still, if speed of processing is not critical, this is a reasonable alternative.

In most cases, it is desirable to display a DR image as soon as possible after acquisition in order to check if patient positioning and exposure level were adequate. In fact, one of the selling features of DR is the ability to (virtually) instantaneously view acquired images—unlike conventional radiography where there are inevitable film processing delays. In order to simplify the design of the correction circuitry but still maintain the ability to instantaneously view images, a "hybrid" approach can be used, i.e., part of the corrections can be done in hardware, and the rest in the host computer. In particular, the offset, drift and zeroth-order gain correction can be done in hardware using equations (1) and (4) and replacing GAIN (ROW) in equation (4) with $A_0$ (ROW). The image data emerging from the hardware are almost fully corrected—lacking only the small first-order gain corrections—and are perfectly acceptable for immediate display for verification of patient positioning and exposure level. The remaining first-order gain correction terms can be applied in the computer later, in an offline mode, producing a fully corrected image for the radiologist to read. The details of such a procedure are not presented here, but would be apparent to designers skilled in the art of mathematics and digital electronics.

The design presented in FIG. 4 could also be replaced by a programmable, high-speed digital signal processor. Alternatively, a computer equipped with an array processor could be programmed to do the calculations. It would also be possible to do some (or all) of the calculations in the analog domain using well-known electronic or optical components.

The particular Taylor series expansion given in equation (1) has been found adequate in the dual energy DR systems investigated so far. However, other representations of the gain functions may also prove to be useful. For example, more terms could be added to the expansion, one could expand about PIX LO/Ref PIX LO and PIX HI/Ref PIX HI instead of LOG (PIX LO/Ref PIX LO) and LOG (PIX HI/Ref PIX HI), and other types of expansions (such as, Fourier series or Chebyshev polynominals) could be used.

Although the system described in detail is a dual energy DR system with an energy discriminating image sensor, the corrections described are equally applicable to any dual energy X-ray system, including those utilizing kVp switching.

If apriori knowledge of the materials being imaged is available, the beam quality can be estimated by making a single transmission measurement. Hence, it is possible to employ an energy dependent gain correction even in a single energy X-ray imaging system. For example, in mammography the materials which are primarily being imaged (soft tissue and fat) are very similar in their X-ray energy attenuation profiles, and the beam hardness can be accurately estimated from single energy pixel values. It would, therefore, be sufficient to measure the gains of the detectors versus pixel value and do a single variable Taylor series expansion. This concept should work, to some degree, even in single energy systems where the materials being imaged are not as uniform as in mammography.

The invention has been described with reference to the preferred embodiment. Obviously, modifications and alterations will occur to others upon reading and understanding the preceding detailed description of the preferred embodiment. It is intended that the invention be construed as including all such alterations and modifications insofar as they come within the scope of the appended claims or equivalents thereof.

Having thus described the preferred embodiment, the invention is now claimed to be:

1. A method of calibrating a dual energy digital radiography system, utilizing a radiation source, a detector array responsive to radiation of at least two different energies spaced from the source to accommodate the placement of an object in a space between the source and detector array, scanning means for effecting relative scanning motion between the detector array and an object when said object is located in said object space, said calibration method comprising the steps of;
    (a) scanning a multiplicity of thicknesses of basis materials to create a matrix of low and high energy pixel data;
    (b) performing a regression on said matrix of low and high energy pixel data to derive at least one low energy coefficient vector and at least one high energy coefficient vector;
    (c) transforming said at least one low energy and at least one high energy coefficient vectors to low and high energy gain functions;
    (d) scanning an examination object to create low and high energy image data;
    (e) combining said low and high energy image data with said low and high energy gain functions to create corrected low and high energy image data.

2. A medical imaging system comprising:
    (a) a radiation source;
    (b) a detector array responsive to incident radiation for producing low and high energy pixel values, said detector array spaced sufficiently from the source to accommodate the interposition of an object in the space between the source and the detector array;
    (c) scanning means for effecting relative scanning motion between the detector array and an object when said object is located in said space between the source and the detector array;
    (d) power means for actuating the source to direct radiation through the object space and toward the detector array;
    (e) circuitry coupled to the detector array for monitoring variations in the low and high energy pixel values caused by variations in the incident beam quality and for producing low and high gain correction signals, said signals being a function of the radiation beam quality and the detector array's response thereto;
    (f) correction means coupled to said detector array and said circuitry for correcting said low and high pixel data values by respectively applying said low and high correction signals to said values; and (g) imaging circuitry coupled to the correction means for producing an image representative of corrected detector array response to incident radiation.

3. The system of claim 2 wherein said circuitry comprises:
(a) means for storing a set of calibration signals representative of variations in detector array response to variations in incident beam quality; and
(b) a function generator coupled to said detector array and said storage means for combining a set of low and high energy image signals representative of radiation transmitted through an object under examination with said calibration signal set to produce low and high gain correction signals.

4. A method of correcting the gain of a radiation detector comprising the steps of:
(a) determining a first detector response by selectively measuring detector response to a beam of radiation transmitted through a multiplicity of thicknesses of basis materials; said radiation being in at least two energy ranges;
(b) determining a representation of the variation in detector gain in response to variations in beam quality of said radiation by performing a regression on said first detector response;
(c) determining a second detector response to radiation transmitted through an object to be imaged;
(d) determining a gain correction factor, said factor a function of said detector gain variation representation and said second detector response; and
(e) combining said second detector response with said gain correction factor.

5. The method of claim 4 wherein said gain correction factor function is represented by a Taylor series expansion.

6. The method of claim 5 wherein said Taylor series expansion is represented by the formula:

$$\text{Gain (PIX LO, PIX HI)} = A_0 + A_1 * \log(\text{PIX LO/Ref PIX LO}) + A_2 * \log(\text{PIX HI/Ref PIX HI})$$

where $A_0$, $A_1$ and $A_2$ are constants of a given detector; PIX LO, PIX HI represent low and hi energy pixel values at a given pixel location; Ref PIX LO, Ref PIX HI represent low and high energy pixel values at a given pixel location at reference beam hardness.

7. A digital radiography system comprising:
(a) a radiation source for directing radiation along a path;
(b) a radiation detector spaced from the source to receive radiation from said source passing through a calibration standard and to produce a first set of signals indicating the detector's response to variations in the beam quality of the incident radiation;
(c) means for storing said first set of signals;
(d) means for producing a gain correction function, said means comprising:
(i) first receiving means coupled to said storage means for receiving said first set of signals;
(ii) second receiving means coupled to the detector for receiving a second set of signals representative of radiation transmitted through an object under examination;
(iii) a function generator for combining said first signal set with said second signal set;
(e) means for combining said second set of signals with said gain correction function to produce gain corrected signals; and
(f) imaging circuitry for receiving said gain corrected signals for producing a representation of the pattern of radiation transmitted through the examination object and incident on the detector.

8. The system of claim 7, wherein said detector comprises:
a plurality of individual detector elements.

9. An imaging system comprising:
(a) a radiation source;
(b) an array of detector elements facing the source each element being responsive to incident radiation to produce electrical signals indicative of said radiation;
(c) circuitry coupled to said detector elements and responsive to said electrical signals for determining the detectors response to variations in the spectral distribution of the incident radiation;
(d) a function generator coupled to said circuitry for producing a detector gain correction signal, said signal being a function of the detectors response to variations in the spectral distribution of the incident radiation;
(e) correction circuitry coupled to said detector elements and to said function generator for generating gain corrected electrical signals by combining the electrical signals and the gain correction signal; and
(f) imaging circuitry coupled to said correction circuitry and responsive to said gain corrected electrical signals for producing a representation of a pattern of said incident radiation.

10. The imaging system of claim 9 wherein the gain corrected electrical signals are generated substantially simultaneously to the production of said incident radiation pattern representation.

11. A dual energy digital x-ray imaging system comprising;
(a) a source of x-radiation;
(b) a dual energy detector array spaced from the source to accommodate an object therebetween, said detector array comprising a first element layer preferentially responsive to low energy x-radiation for producing low energy pixel data and a second element layer preferentially responsive to high energy x-radiation for producing high energy pixel data;
(c) logger means for generating the logarithm of said low energy pixel data and said high energy pixel data;
(d) means for storing first, second and third high energy coefficients and first, second and third low energy coefficients;
(e) sum of products calculator means for producing;
(i) a high energy gain correction signal derived from the sum of the product of the first high energy coefficient and the logarithm of the low energy pixel data plus the product of the second high energy coefficient and the logarithm of the high energy pixel data plus the third high energy coefficient; and
(ii) a low energy gain correction signal derived from the sum of the product of the first low energy coefficient and the logarithm of the low energy pixel data plus the product of the second low energy coefficient and the logarithm of the high energy pixel data plus the third low energy coefficient;
(f) multiplier means for producing;
  (i) corrected high energy pixel data by multiplying the high energy pixel data by the high energy gain correction signal; and
  (ii) corrected low energy pixel data by multiplying the low energy pixel data by the low energy gain correction signal; and
(g) display means for displaying an image representative of at least one of said corrected low energy pixel data and said high corrected energy pixel data.

12. The imaging system of claim 11 wherein said first, second and third, low and high energy coefficients are constants of the first and second element layers, respectively.

13. The imaging system of claim 12 wherein said constants of the first and second element layers are determined through a basis calibration.

14. A dual energy digital x-ray imaging system comprising;
(a) means for producing at least a high energy radiation spectrum and a low energy radiation spectrum;
(b) a radiation detector responsive to said radiation spectra for producing low energy pixel data and high energy pixel data;
(c) logger means for generating the logarithm of said low energy pixel data and said high energy pixel data;
(d) means for storing first, second and third high energy coefficients and first, second and third low energy coefficients;
(e) sum of products calculator means for producing;
  (i) a high energy gain correction signal derived from the sum of the product of the first high energy coefficient and the logarithm of the low energy pixel data; the product of the second high energy coefficient and the logarithm of the high energy pixel data; and the third high energy coefficient; and
  (ii) a low energy gain correction signal derived from the sum of the product of the first low energy coefficient and the logarithm of the low energy pixel data; the product of the second low energy coefficient and the logarithm of the high energy pixel data; and the third low energy coefficient;
(f) multiplier means for producing;
  (i) corrected high energy pixel data by multiplying the high energy pixel data by the high energy gain correction signal; and
  (ii) corrected low energy pixel data by multiplying the low energy pixel data by the low energy gain correction signal; and
(g) display means for displaying an image representative of at least one of said corrected low energy pixel data and said corrected high energy pixel data.

15. The imaging system of claim 14 wherein said first, second and third, low and high energy coefficients are constants of the radiation detector.

16. The imaging system of claim 15 wherein said constants of the radiation detector are determined through a basis calibration.

17. The system of claim 14 wherein said means of producing the radiation spectra comprises an x-ray tube operating at multiple energy levels.

18. The system of claim 14 wherein said detector is spaced from the radiation producing means to accommodate an object therebetween.

19. A method of calibrating a dual energy radiation imaging system utilizing a radiation source for directing radiation along a beam path, a radiation detector positioned in the beam path and spaced from the source to accommodate the placement of an object therebetween, said detector responsive to radiation incident thereon and capable of producing high energy and low energy pixel signals representative of said incident radiation, said method comprising the steps of:
(a) placing a multiplicity of thicknesses of basis materials in the space between the source and detector;
(b) directing radiation through said basis materials;
(c) monitoring the high energy and low energy pixel signals produced by said detector in response to radiation passing through said basis materials;
(d) transforming said high energy and low energy pixel signals monitored in step (c) into high energy and low energy transfer functions;
(e) replacing said basis materials with an object to be examined;
(f) directing radiation through the object to be examined;
(g) monitoring the high energy and low energy pixel signals produced by said detector in response to radiation passing through said object to be examined;
(h) combining in a predetermined way said high energy low energy pixel signals monitored in step (g) with the high energy transfer functions to produce a high energy correction factor;
(i) combining in a predetermined way said high energy and low energy pixel signals monitored in step (g) with the low energy transfer function to produce a low energy correction factor;
(j) combining the high energy pixel value monitored in step (g) with the high energy correction factor to produce corrected high energy pixel data; and
(k) combining the low energy pixel value monitored in step (g) with the low energy correction factor to produce corrected low energy pixel data.

20. The method of claim 19 wherein the step of transforming comprises performing a regression on said high energy and low energy pixel signals monitored in step (c).

21. The method of claim 19 wherein the steps of combining in a predetermined way comprise a Taylor series expansion.

* * * * *